United States Patent [19]

Anderson

[11] Patent Number: 4,966,165
[45] Date of Patent: Oct. 30, 1990

[54] UNISEX CONDOM

[76] Inventor: Ray C. Anderson, 7605 S. Quebec, Tulsa, Okla. 74136

[21] Appl. No.: 212,244

[22] Filed: Aug. 12, 1988

Related U.S. Application Data

[63] Continuation-in-part of Ser. No. 47,121, May 8, 1987, abandoned.

[51] Int. Cl.⁵ .............................................. A61F 5/42
[52] U.S. Cl. ..................................... 128/830; 128/844; 604/349
[58] Field of Search ..................... 128/830, 842–844; 604/349–353

[56] References Cited

U.S. PATENT DOCUMENTS

D. 288,485  2/1987  Denno .................................. D24/51
3,536,066  10/1970  Ludwig .......................... 604/353 X
4,664,104  5/1987  Jaicks .............................. 604/353 X
4,807,611  2/1989  Johnson ............................. 128/844

FOREIGN PATENT DOCUMENTS 117234  10/1926  Switzerland ....................... 604/349

Primary Examiner—Dalton L. Truluck

[57] ABSTRACT

A unisex condom to be worn as an underpant type garment with pocket or shaft type depressions or tubular extensions in the lower front and lower rear. During use the tubular extensions can be inserted inside the lower body cavities, vagina and anus or may be reversed or turned inside out for placement as a covering or exterior liner for a penis. This total covering of body parts will more fully protect the user from contacting or spreading disease as the result of sexual activities.

5 Claims, 1 Drawing Sheet

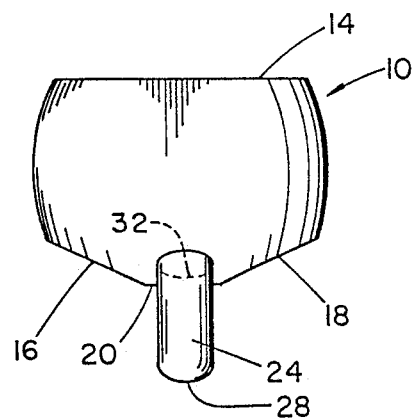
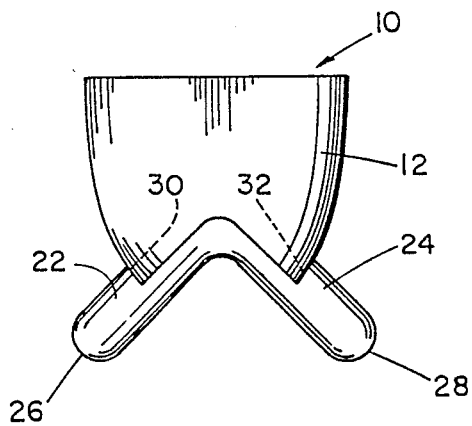
FIG. 1   FIG. 2
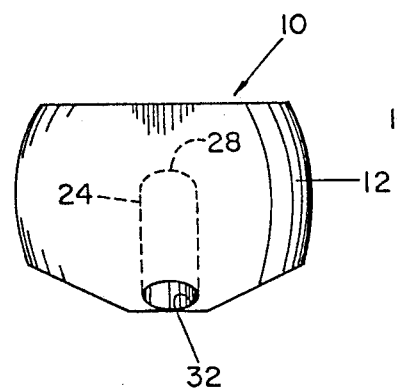
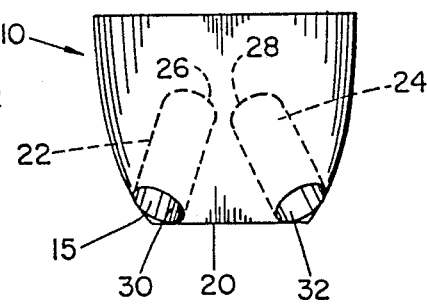
FIG. 3   FIG. 4
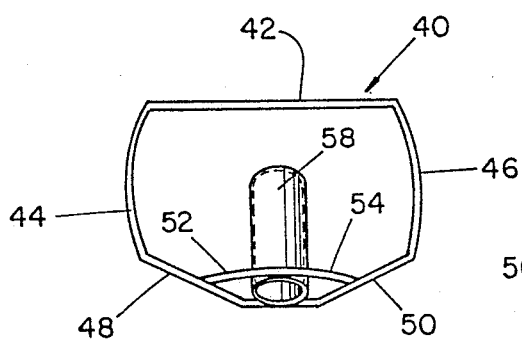
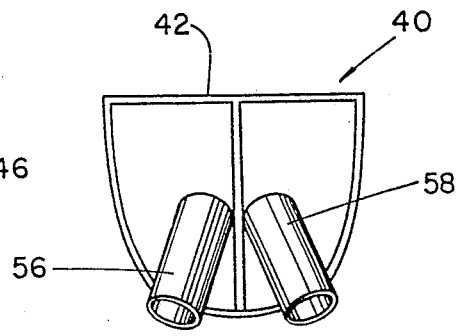
FIG. 5   FIG. 6

UNISEX CONDOM

This is a continuation of U.S. patent application Ser. No. 047,121, filed May 8, 1987, now abandoned.

FIELD OF THE INVENTION

This invention relates generally to condoms for use in the prevention of disease transmission between humans as the result of sexual activities. More specifically, the present invention is related to an integral condom device that may be worn by either a male or female during sexual activities of heterosexual or homosexual nature for the purpose of preventing transmission from one person to another of any one of a number of diseases that can be transmitted between human partners engaged in sexual activities

BACKGROUND OF THE INVENTION

The invention relates generally to the use of condoms and more particularly to condom protection of the vagina, anus, penis and scrotum.

Condoms used for disease protection are most normally made for penis covering only. The condom is rolled over a normally erected penis and the covering offers some protection. At times this type of condom slips off the penis during intercourse and thereby loses all protection desired It is desirable to provide a condom device that may be worn by either males or females, which is efficiently and positively supported in place during sexual activities and which provides absolute protection against transfer of body fluids from or to the user during sexual intercourse.

SUMMARY OF THE INVENTION

It is an object of the present invention to provide a male or a female with complete protection from disease being transmitted in the areas of the penis, vagina, anus or in the genital area by providing protective covering of the walls of the vagina, anus, penis and the genital area with an integral condom unit.

Briefly, an integral condom structure is provided that is adapted to fit in substantially skin tight manner about the pelvic region of a human male or female. In one form of the invention, the integral unisex condom is in the form of pants or briefs defining openings for the waist and legs of the user. The condom device also defines a pair of tubular projections that are integral with the condom structure and have closed ends. These projections may extend externally of the device such as in the case for use by males or may be reversed and extend internally of the device such as for use by females or males.

In another form of the invention, the unisex condom device is defined by a plurality of inter connected straps that are intended to fit about the pelvic region of the user. A pair of tubular projections are formed integrally with and extend from the straps and define an open end and a closed end, the open end being interconnected with one or more of the straps. In this case the tubular elements may project externally such as for use by males or may be reversed and project internally such as for use by males and females as linings for body openings.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

In the drawings:

FIG. 1 is a front elevational view of a unisex condom constructed in accordance with the present invention;

FIG. 2 is a side elevational view of the device of FIG. 1;

FIG. 3 is a front elevational view of the device of FIG. 1 with the tubular projections thereof shown in broken lines to be reversed and projecting inwardly:

FIG. 4 is a side elevational view of the device of FIGS. 1 and 2 with the tubular projections shown by broken lines to be reversed and positioned inwardly for internal use;

FIG. 5 is a front elevational view of a unisex condom device representing an alternative embodiment of the present invention and in broken lines showing the tubular projections thereof reversed and positioned inwardly for internal use; and FIG. 6 is a side elevational view of the device of FIG. 5 showing the front and rear tubular projections thereof reversed and positioned inwardly for internal use.

DETAILED DESCRIPTION OF PREFERRED EMBODIMENT

Referring now to the drawings and first to FIGS. 1 and 2 an integral unisex condom structure is illustrated generally at 10 which comprises a body portion 12 in the general form of a pant or brief formed of flexible material that is impermeable to liquids and gases and which is adapted to be worn in close fitting relation about the pelvic region of the user. The body structure 12 forms an upwardly directed opening 14 adapted to receive the waist or pelvic region of the user and defines a pair of spaced openings 16 and 18 at the lower portion thereof through which the legs of the user will extend. The body structure also forms a lower panel or section 20 that is positioned in the crotch region between the legs of the user.

From the crotch region of the device extend a pair of elongated tubular elements 22 and 24 that are integral with the body structure 12 and which define rounded closed ends 26 and 28 respectively. The tubular projections 22 and 24 define respective openings 30 and 32 that open into the internal area of the briefs or pants and thus permit the penis of a male user to be received in either of the tubular pockets defined by the tubular projections, depending upon the position of the condom device on the user. As shown in FIGS. 1 and 2, the tubular projections 22 and 24 are shown to extend downwardly and outwardly from opposite sides of the body structure 12. As shown in FIGS. 3 and 4 the tubular projections 22 and 24 are shown to be reversed and positioned inwardly such that the projections are adapted to be received as linings within desired body openings of the user. Since the tubular projections are integral with the body structure of the condom device the tubular projections will be effectively supported against becoming inadvertently dislodged from the penis of a male or the body openings of males or females. Further the condom will cover the entire genital area of the user, whether male or female, and thus provides absolute protection against transfer of body fluids to or from the user.

Referring now to FIGS. 5 and 6 an alternative embodiment of the present invention is disclosed which is also adapted to be worn about the pelvic region of the user. In this case, the device shown generally at 40 incorporates a waist band 42 which is of generally circular form and is intended to be positioned about the waist or pelvic region of the user. From the waist band extends a pair of side straps 44 and 46. Other straps may also extend from the waist band 42 as desired to provide appropriate support for tubular projections or condom elements of the device. Below and integrally connected with the side straps 44 and 46 and, if desired, connected to other straps, are positioned a pair of leg encircling straps 48 and 50 which are adapted to fit in encircling relation about the upper thigh portion of the legs of the user. Reinforcing strap elements 52 and 54 are formed integrally with and extend from the leg encircling straps 48 and 50 to the tubular projections.

The pair of tubular condom elements 56 and 58 are also formed integrally with the strap structure such that the respective straps provide efficient support for the tubular condom elements. As shown in FIG. 6, the condom elements 56 and 58 are disposed in angular relation with one another and may be positioned to project inwardly as shown in FIGS. 5 and 6 such as for use by male or female users or to be reversed and project outwardly in the manner shown generally in FIGS. 1 and 2 such as for use by male users.

While the foregoing is directed to the preferred embodiment of the present invention, other and further embodiments of the invention may be devised without departing from the basic scope thereof, and the scope thereof is determined by the claims which follow.

What is claimed is:

1. A unisex condom to be worn by human males or females, comprising:
   (a) pant-like body means adapted to be received about the pelvic region of a human male or female user and forming front, rear and side portions and a crotch portion, said body means defining a waist opening at the upper portion thereof and a pair of leg openings at the lower portion thereof; and
   (b) a pair of impervious flexible tubular projections formed integrally with and extending from the front and rear of said crotch portion of said body means and being disposed in angular relation with one another, said tubular projections each defining a closed extremity and each forming a respective opening at the juncture thereof with said body means, and are capable of being reversed inside-out to thereby position at least one of said projections inwardly of said body means.

2. A unisex condom as recited in claim 1, wherein:
   said body structure and said tubular projections are formed from rubber-like material that is impermeable to gases and liquids.

3. A unisex condom for use by males or females comprising:
   (a) a plurality of condom support straps interconnected together and forming an upper opening to be received about the waist or pelvic region of the user and a pair of leg openings adapted to receive the upper thigh portion of the legs of the user;
   (b) condom support straps being interconnected with said straps forming said leg openings; and
   (c) a pair of flexible tubular condom elements each composed of a material that is imperforate to gases and liquids being secured to said condom support straps and extending respectively forwardly and rearwardly of said leg openings, said tubular condom elements being disposed in angular relation with one another, said condom elements being of flexible nature and may be reversed inwardly and adapted to be received within body openings of both male and female users.

4. A unisex condom as recited in claim 2 wherein:
   said condom support straps and said tubular condom elements are formed integrally from a flexible sheet material that is impenetrable by liquids and gases.

5. A unisex condom as recited in claim 3, wherein:
   said condom support straps are formed integrally with and extend between said waist encircling straps and said leg encircling straps.

* * * * *